United States Patent
Rizkala et al.

(10) Patent No.: US 11,058,667 B2
(45) Date of Patent: Jul. 13, 2021

(54) SACUBITRIL-VALSARTAN DOSAGE REGIMEN FOR TREATING HEART FAILURE

(71) Applicant: Novartis AG, Basel (CH)

(72) Inventors: Adel Remond Rizkala, East Brunswick, NJ (US); Victor Chengwei Shi, Mendham, NJ (US); Fabian Chen, Englewood Cliffs, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/572,399

(22) PCT Filed: May 9, 2016

(86) PCT No.: PCT/IB2016/052633
§ 371 (c)(1),
(2) Date: Nov. 7, 2017

(87) PCT Pub. No.: WO2016/181284
PCT Pub. Date: Nov. 17, 2016

(65) Prior Publication Data
US 2018/0125820 A1 May 10, 2018

Related U.S. Application Data

(60) Provisional application No. 62/159,703, filed on May 11, 2015.

(51) Int. Cl.
*A61K 31/41* (2006.01)
*A61K 31/225* (2006.01)
*A61P 9/04* (2006.01)

(52) U.S. Cl.
CPC ............ *A61K 31/41* (2013.01); *A61K 31/225* (2013.01); *A61P 9/04* (2018.01); *A61K 2300/00* (2013.01)

(58) Field of Classification Search
CPC .. A61K 31/41; A61K 31/225; A61K 2300/00; A61P 9/04
See application file for complete search history.

(56) References Cited

FOREIGN PATENT DOCUMENTS

WO WO-2014029848 A1 * 2/2014 ........... A61K 31/194

OTHER PUBLICATIONS

NCT01922089—version from Nov. 20, 2013 (v3) retrieved Jul. 16, 2018 (Year: 2013).*

Kobalava et al., "First Experience with Concomitant ATI and Neprilysin (NEP 24.11) Inhibition with LCZ696 in Patients with Chronic Heart Failure", Circulation, vol. 122, No. 21 (supplement), A19278, Nov. 23, 2010 (Nov. 23, 2010).

McMurray et al., "Dual angiotensin receptor and neprilysin inhibition as an alternative to angiotensin-converting enzyme inhibition in patients with chronic systolic heart failure: rationale for and design of the Prospective comparison of ARNI with ACEI to Determine Impact", European Journal of Heart Failure, vol. 15, No. 9, Apr. 5, 2013 (Apr. 5, 2013)., pp. 1062-1073.

McMurray et al., "Angiotensin-Neprilysin Inhibition versus Enalapril in Heart Failure", New England Journal of Medicine, vol. 371, No. 11, Sep. 11, 2014 (Sep. 11, 2014), pp. 993-1004.

Gu et al., "Pharmacokinetics and pharmacodynamics of LCZ696, a novel dual-acting angiotensin receptor-neprilysin inhibitor (ARNi)", Journal of Clinical Pharmacology, vol. 50, No. 4, Apr. 1, 2010 (Apr. 1, 2010), pp. 401-414.

Kario et al., "LCZ696, a First-in-Class Angiotensin Receptor-Neprilysin Inhibitor: The First Clinical Experience in Patients With Severe Hypertension", The Journal of Clinical Hypertension. vol. 18, No. 4, Sep. 24, 2015 (Sep. 24, 2015), pp. 308-314.

Anonymous: "Entresto Prescribing Information", Aug. 1, 2015 (Aug. 1, 2015) [Retrieved from the Internet: URL: ttps://www.pharma.us.novartis.com/sites/www.pharma.us.novartis.com/files/entresto.pdf] [retrieved on Jun. 16, 2016] See section 2.1: Dosing [retrieved on Jun. 16, 2016].

Anonymous:"Safety and Tolerability of Initiating LCZ696 in Heart Failure Patients—Full Text View—ClinicalTrials.gov", Aug. 12, 2013 (Aug. 12, 2013), [Retrieved from the Internet: URL:https://clincaltrials.gov/jct2/show/NCT01922089?term=NCT01922089&rank=1] [retrieved on Jun. 16, 2016].

Solomon, et al., "The angiotensin receptor neprilysin inhibitor LCZ696 in heart failure with preserved ejection fraction: a phase 2 double-blind randomised controlled trial", Lancet, 380:1387-95. 2012.

Senni et al., "Initiating sacubitril/valsartan (LCZ696) in heart failure: results of Titration, a double-blind, randomized aomparison of two uptitration regimens", including Supplemental Appendix p. 1-9, European Journal of Heart Failure (May 12, 2016) 18, 1193-1202.

Entresto Dosing and Titration Guide (2019).
Entresto Prescribing information (Jul. 2015).
Entresto Dosing and Titration Guide (2017).
Entresto Dosing and Titration Guide (2015).
Entresto Dosing and Safety, https://www.entrestohcp.com/dosing-and-safety (2020).

"Titration study confirms LCZ696 safe and tolerated in clinical practice. More than 70% of HFrEF patients achieved the target dose", European Society of Cardiology Press release (May 23, 2015).

Brauser, "Titration: Two LCZ696 Dosing Regimens Appear Safe, Tolerable for Range of HFrEF Patients", Medscape (May 25, 2015).

* cited by examiner

*Primary Examiner* — Sarah Pihonak
*Assistant Examiner* — Jason Deck
(74) *Attorney, Agent, or Firm* — Meghan S. Adams (57) ABSTRACT

The present invention relates to sacubitril-valsartan dosage regimens for the treatment of heart failure in a patient.

19 Claims, 1 Drawing Sheet

SACUBITRIL-VALSARTAN DOSAGE REGIMEN FOR TREATING HEART FAILURE

RELATED APPLICATIONS

This application is a national stage application, filed under 35 U.S.C. § 371, of International Application No. PCT/IB2016/052633, filed May 9, 2016, which claims priority to and the benefit of U.S. Provisional Application No. 62/159,703, filed May 11, 2015, the entire contents of each of which are incorporated herein by reference in their entireties.

FIELD OF THE INVENTION

The present invention relates to novel methods and pharmaceutical compositions for the treatment of heart failure in a patient, in particular to a regimen for treating heart failure which comprises administering to a patient in need thereof a twice-daily target dose of an Angiotensin Receptor Neprilysin inhibitor (ARNi) or of a combination of an Angiotensin Receptor Blocker (ARB) with a Neutral Endopeptidase inhibitor (NEPi) or with a NEPi pro-drug, wherein said target dose is reached after a titration with an initial lower twice-daily dose of said ARNI increasing to the twice daily target dose from about 2 to about 8 weeks.

BACKGROUND OF THE INVENTION

Chronic heart failure (CHF) is a major public health problem characterized by significant mortality, frequent hospitalization, and poor quality of life, with an overall prevalence that is increasing throughout the world. In the United States (US) alone, approximately 5 million patients have heart failure (HF) and there are over half a million newly diagnosed cases annually. In Europe, the prevalence of HF is between 2 and 3%, and that in the elderly is estimated between 10 to 20%.

Medical therapies targeted at improving outcomes in HF with a low LVEF have been well studied over the past two decades, leading to an improvement in survival as well as a decrease in morbidity, mostly in the form of decrease in re-hospitalization for HF. These medical therapies include angiotensin converting enzyme (ACE) inhibitors, angiotensin receptor blockers (ARBs), β-blockers and mineralocorticoid antagonists.

However, despite advances in pharmacological (and device therapies), the outlook remains poor. Overall 50% of patients die within 4 years, and 40% of patients admitted to hospital with HF die or are readmitted within 1 year. Thus, HF still represents a major cause of cardiac mortality and morbidity with a clear need for better therapy.

LCZ696 is a first-in-class, angiotensin receptor neprilysin inhibitor (ARNI) being developed for the treatment of CHF. Following ingestion, LCZ696 provides systemic exposure to sacubitril (AHU377; (2R,4S)-5-biphenyl-4-yl-4-(3-carboxy-propionylamino)-2-methyl-pentanoic acid ethyl ester, also named N-(3-carboxy-1-oxopropyl)-(4S)-(p-phenylphenylmethyl)-4-amino-2R-methylbutanoic acid ethyl ester), a neprilysin (neutral endopeptidase 24.11, NEP) inhibitor (NEPi) and valsartan, an ARB, in a 1:1 molar ratio. AHU377 is further metabolized via esterases to the active NEPi, LBQ657. Neprilysin degrades biologically active natriuretic peptides (NPs), including atrial natriuretic peptide (ANP), B-type natriuretic peptide (BNP) and C-type natriuretic peptide (CNP). The effects of NEP inhibition are attributed to the enhanced effects of biologically active NPs. NPs, acting through the second messenger cyclic guanosine monophosphate, have potent natriuretic and vasodilator properties, inhibit the activity of the renin-angiotensin-aldosterone system (RAAS), lower sympathetic drive and have anti-fibrotic and anti-hypertrophic effects. Angiotensin receptor blockade is specific and competitive at the angiotensin type 1 (AT1) receptor, which mediates the deleterious effects of angiotensin II on the cardiovascular system. LCZ696, through its dual mode of action, potentiates NPs via NEP inhibition while inhibiting the RAS via AT1 receptor blockade. Both of these mechanisms are considered to act in a complementary and additive manner to improve the morbidity and mortality of HF patients.

The clinical efficacy of LCZ696 in reducing the cardiovascular death and hospitalizations due to HF in HF-rEF patients was assessed in the LCZ696B2314 PARADIGM-HF study. The PARADIGM-HF study incorporated a single-blind, active run-in phase that was designed to assure a large proportion of patients will maintain target dose study drug during the long term study. Patients entered a single-blind active run-in in which they received enalapril 10 mg bid, followed by LCZ696 100 mg bid, and then LCZ696 200 mg bid. Patients must tolerate the study target dose of enalapril (10 mg bid) and the study target dose of LCZ696 (200 mg bid) for at least 2 weeks in order to be randomized. However, the active run-in phase included in the PARADIGM-HF study design (the sequential use of enalapril followed by LCZ696) provided limited information on how the physician should initiate the LCZ696 therapy in clinical practice, in particular for those patients who are currently on the low dose of ACEIs or ARBs, or ACEI/ARB-naïve patients.

Accordingly there was a need to provide guidance on dosing and up-titration of LCZ696 (sacubitril and valsartan in a 1:1 molar ratio).

The compounds and pharmaceutical compositions disclosed herein include novel drug candidates potentially useful for the treatment of hypertension and/or heart failure. Such compounds or pharmaceutical compositions have been previously disclosed in WO 2003/059345, WO 2007/056546, WO 2009/061713 as well as WO2014029848, which are herein incorporated by reference.

SUMMARY OF THE INVENTION

Surprisingly, it has been shown with a regimen for treating heart failure which comprises administering to a patient in need thereof a twice-daily target dose of 200 mg of sacubitril and valsartan in a 1:1 molar ratio (e.g. LCZ696), wherein said target dose is reached after a titration with an initial twice-daily dose of at least 50 mg of sacubitril and valsartan in a 1:1 molar ratio increasing to the twice daily target dose of 200 mg of from about 2 to about 8 weeks, the target dose can be safely reached in the large majority of the patients.

The treatment success rate with sacubitril and valsartan in a 1:1 molar ratio (e.g. LCZ696) was even more improved if patients taking lower doses of ACEIs/ARBs (i.e., the low RAAS stratum) were up-titrated more gradually than patients who were taking higher doses of ACEIs/ARBs. The treatment success rate was 10% higher (85%) for patients in the low RAAS stratum given gradual up-titration over 6 weeks compared to those given condensed up-titration over 3 weeks. This difference was due to hypotension, hyperkalemia and renal dysfunction in most cases. On the other hand, surprisingly, there was no difference in the treatment success rate for high RAAS stratum patients, regardless of the rate of up-titration (3 weeks vs. 6 weeks).

Accordingly, the present invention, in a first embodiment relates to a regimen for treating heart failure which comprises administering to a patient in need thereof a twice-daily target dose of 200 mg of sacubitril and valsartan in a 1:1 molar ratio, wherein said target dose is reached after a titration with an initial twice-daily dose of at least 50 mg of sacubitril and valsartan in a 1:1 molar ratio increasing to the twice daily target dose of 200 mg of from about 2 to about 8 weeks.

In one embodiment thereof, the patient is a human patient.

In another embodiment thereof, the compound of formula (I) is trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

In another embodiment, the present invention relates to a regimen for treating heart failure which comprises administering to a patient in need thereof a twice-daily target dose of 200 mg of sacubitril and valsartan in a 1:1 molar ratio, wherein said dose is reached after a titration with a twice daily starting dose of 50 mg of sacubitril and valsartan in a 1:1 molar ratio for from about 2 weeks to about 4 weeks, followed by a twice daily dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter, and wherein the twice daily starting dose of 50 mg of sacubitril and valsartan in a 1:1 molar ratio is for use in a patient not taking an angiotensin-converting enzyme (ACE) inhibitor or an angiotensin II receptor blocker (ARB) before initiating the treatment with sacubitril and valsartan.

In another embodiment, the present invention relates to a regimen for treating heart failure which comprises administering to a patient in need thereof a twice-daily target dose of 200 mg of sacubitril and valsartan in a 1:1 molar ratio, wherein said dose is reached after a titration with a twice daily starting dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter and wherein the twice daily starting dose of 100 mg of sacubitril and valsartan in a 1:1 molar ratio is for use in a patient taking higher doses of an angiotensin-converting enzyme (ACE) inhibitor or of an angiotensin II receptor blocker (ARB) before initiating the treatment with sacubitril and valsartan.

In another embodiment, the present invention relates to a twice-daily target dose of 200 mg of sacubitril and valsartan in a 1:1 molar ratio for use in the treatment of heart failure in a patient, wherein said dose is reached after a titration with an initial twice-daily dose of at least 50 mg of sacubitril and valsartan in a 1:1 molar ratio increasing to the twice daily target dose of 200 mg for from about 2 to about 8 weeks.

In another embodiment, the present invention is directed to the use of sacubitril and valsartan in a 1:1 molar ratio for the manufacture of a medicament for the treatment of heart failure in a patient, wherein the medicament comprises a twice-daily target dose of 200 mg of sacubitril and valsartan in a 1:1 molar ratio which is reached after a titration with an initial twice-daily dose of at least 50 mg of sacubitril and valsartan in a 1:1 molar ratio increasing to the twice daily target dose of 200 mg for from about 2 to about 8 weeks.

Definitions

Throughout this specification and in the claims that follow, the following terms are defined with the following meanings, unless explicitly stated otherwise.

The term "prevention" refers to prophylactic administration to a healthy subject to prevent the development of the conditions mentioned herein. Moreover, the term "prevention" means prophylactic administration to patients being in a pre-stage of the conditions to be treated.

The term "treatment" is understood the management and care of a patient for the purpose of combating the disease, condition or disorder.

The term "therapeutically effective amount" refers to an amount of a drug or a therapeutic agent that will elicit the desired biological and/or medical response of a tissue, system or an animal (including man) that is being sought by a researcher or clinician.

The terms "patient" include, but are not limited to, humans, dogs, cats, horses, pigs, cows, monkeys, rabbits and mice. The preferred patients are humans.

The terms "administration of" and or "administering a" compound should be understood to mean providing a compound of the invention or a pharmaceutically acceptable salt or ester thereof, or a pro-drug thereof to a subject in need of treatment. The administration of the composition of the present invention in order to practice the present methods of therapy is carried out by administering a therapeutically effective amount of the compounds in the composition to a subject in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgment.

The term "prophylactically effective amount" as used herein means the amount of the active compounds in the composition that will elicit the biological or medical response in a tissue, system, subject, or human that is being sought by the researcher, veterinarian, medical doctor or other clinician, to prevent the onset of a disease characterized and/or manifested by atrial enlargement and/or remodeling.

The term "pharmaceutically acceptable", as used herein, refers to those compounds, materials, compositions and/or dosage forms, which are, within the scope of sound medical judgment, suitable for contact with the tissues of mammals, especially humans, without excessive toxicity, irritation, allergic response and other problem complications commensurate with a reasonable benefit/risk ratio.

The New York Heart Association (NYHA) classification grades the severity of heart failure symptoms as one of four functional classes. The NYHA classification is widely used in clinical practice and in research because it provides a standard description of severity that can be used to assess response to treatment and to guide management. The New York Heart Association functional classification based on severity of symptoms and physical activity:

Class I: No limitation of physical activity. Ordinary physical activity does not cause undue breathlessness, fatigue, or palpitations.

Class II: Slight limitation of physical activity. Comfortable at rest, but ordinary physical activity results in undue breathlessness, fatigue, or palpitations.

Class III: Marked limitation of physical activity. Comfortable at rest, but less than ordinary physical activity results in undue breathlessness, fatigue, or palpitations.

Class IV: Unable to carry on any physical activity without discomfort. Symptoms at rest can be present. If any physical activity is undertaken, discomfort is increased.

Choice of endpoints: Cardiovascular death and heart failure hospitalization both reflect disease-specific endpoints related to progressive worsening of the heart failure syndrome, and experienced by patients with systolic heart failure. These endpoints can be modified by treatments improving this condition, which has generally proved to be the case with drugs such as ACEIs, aldosterone antagonists, and 3-blockers as well as devices for cardiac resynchronization therapy.

In the context of the present invention, the term "sacubitril and valsartan in a 1:1 molar ratio" refers to an Angiotensin Receptor Neprilysin inhibitor (ARNi) which is
a) trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), or
b) a combination comprising a therapeutically effective amount of a 1:1 molar ratio of
   (i) valsartan or a pharmaceutically acceptable salt thereof; and
   (ii) sacubitril or a pharmaceutically acceptable salt thereof.

DETAILED DESCRIPTION OF THE INVENTION

This invention has shown based on the clinical trial TITRATION (see Example section) that the large majority of patients initiated on a treatment with sacubitril and valsartan in a 1:1 molar ration achieved and maintained the target dose of 200 mg twice daily without any dose interruption or down-titration over 12 weeks. More patients who were naïve to previous ACE inhibitor or ARB therapy or on low-dose therapy (equivalent to <10 mg enalapril/day) were able to achieve and maintain the 200 mg target dose when up-titrated over 6 weeks versus 3 weeks.

Accordingly, the present invention relates to the following:

Methods of Treatment

Embodiment 1

The invention encompasses a regimen for treating heart failure which comprises administering to a patient in need thereof a twice-daily target dose of 200 mg of sacubitril and valsartan in a 1:1 molar ratio, wherein said target dose is reached after a titration with an initial twice-daily dose of at least 50 mg of sacubitril and valsartan in a 1:1 molar ratio increasing to the twice daily target dose of 200 mg of from about 2 to about 8 weeks.

The invention is further described in the following embodiments, numbered 2 to 20:

2. A regimen for treating heart failure according to embodiment 1, wherein said dose is reached after a titration with a twice daily starting dose of 50 mg of sacubitril and valsartan in a 1:1 molar ratio for from about 2 weeks to about 4 weeks, followed by a twice daily dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

3. A regimen for treating heart failure according to embodiment 2, wherein said dose is reached after a titration with a twice daily starting dose of 50 mg of sacubitril and valsartan in a 1:1 molar ratio for from about 2 weeks to about 3 weeks, followed by a twice daily dose of 100 mg of sacubitril and valsartan in a 1:1 molar ratio for about 3 weeks, followed by the twice daily target dose of 200 mg of sacubitril and valsartan in a 1:1 molar ratio thereafter.

4. A regimen for treating heart failure according to embodiment 1, wherein said dose is reached after a titration of a twice daily starting dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

5. A regimen for treating heart failure according to embodiment 4, wherein said dose is reached after a titration of a twice daily starting dose of 100 mg of sacubitril and valsartan in a 1:1 molar ratio for about 2 weeks, followed by the twice daily target dose of 200 mg of sacubitril and valsartan in a 1:1 molar ratio thereafter.

6. A regimen for treating heart failure according to embodiment 2 or 3, wherein the twice daily starting dose of 50 mg of sacubitril and valsartan in a 1:1 molar ratio is for use in a patient not taking an angiotensin-converting enzyme (ACE) inhibitor or an angiotensin II receptor blocker (ARB) before initiating the treatment with sacubitril and valsartan.

7. A regimen for treating heart failure according to embodiment 2, wherein the twice daily starting dose of 50 mg of sacubitril and valsartan in a 1:1 molar ratio is for use in a patient taking low doses of an angiotensin-converting enzyme (ACE) inhibitor or of an angiotensin II receptor blocker (ARB) before initiating the treatment with sacubitril and valsartan.

8. A regimen for treating heart failure according to embodiment 7, wherein the lower dose of an ACEI or ARB is equivalent to <10 mg of enalapril per day.

9. A regimen for treating heart failure according to embodiment 1, wherein said titration mitigates a risk selected from hypotension, hyperkalemia, and renal adverse events.

10. A regimen for treating heart failure according to embodiment 4 or 5, wherein the twice daily starting dose of 100 mg of sacubitril and valsartan in a 1:1 molar ratio is for use in a patient taking higher doses of an angiotensin-converting enzyme (ACE) inhibitor or of an angiotensin II receptor blocker (ARB) before initiating the treatment with sacubitril and valsartan.

11. A regimen for treating heart failure according to embodiment 10, wherein the higher dose of an ACEI or ARB is equivalent to ≥10 mg of enalapril per day.

12. A regimen for treating heart failure according to embodiment 1, wherein the patient suffers from chronic systolic heart failure with reduced ejection fraction.

13. A regimen for treating heart failure according to embodiment 1, wherein the patient is a human patient.

14. A regimen for treating heart failure according to embodiment 1, wherein the patient has at least one of the following characteristics
   i) heart failure of NYHA class II, III or IV, ii) an elevated plasma BNP or NT-proBNP level, preferably a plasma BNP ≥100 pg/mL (or NT-proBNP ≥400 pg/mL), more preferably a plasma BNP ≥150 pg/mL or NT-proBNP ≥600 pg/mL, and iii) a reduced left ventricular ejection fraction (LVEF) of ≤40%, preferably ≤35%.

15. A regimen for treating heart failure according to embodiment 1, wherein the patient suffers from chronic heart failure classified as NYHA class II, III or IV and has systolic dysfunction, preferably wherein the patient has a reduced left ventricular ejection fraction (LVEF) of ≤35%.

16. A regimen for treating heart failure according to embodiment 1, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate]hemipentahydrate (LCZ696).

17. A regimen for treating heart failure according to embodiment 1, wherein sacubitril and valsartan in a 1:1 molar ratio are delivered in the form of a pharmaceutical composition comprising
    (i) valsartan or a pharmaceutically acceptable salt thereof; and
    (ii) sacubitril or a pharmaceutically acceptable salt thereof, 18. A regimen for treating heart failure according to embodiment 1, wherein the patient receives a base treatment with a stable dose of a beta-blocker, an aldosterone antagonists, and/or a diuretic.

19. A regimen for treating heart failure according to embodiment 1, wherein the patient has to stop taking the angiotensin receptor blocker (ARB) or the ACE inhibitor at least 36 hours prior to taking the medicament.

20. A regimen for treating heart failure according to embodiment 1, wherein
    a) the 50 mg dose of sacubitril and valsartan in a 1:1 molar ratio corresponds to 24 mg sacubitril and 26 mg valsartan,
    b) the 100 mg dose of sacubitril and valsartan in a 1:1 molar ratio corresponds to 49 mg sacubitril and 51 mg valsartan, and
    c) the 200 mg dose of sacubitril and valsartan in a 1:1 molar ratio corresponds to 97 mg sacubitril and 103 mg valsartan.

In another embodiment of the foregoing, the patient is a human patient.

In another embodiment of the foregoing, the patient suffering from chronic systolic heart failure, in particular the patient with chronic systolic heart failure with reduced ejection fraction, has at least one of the following characteristics:
    i) heart failure of NYHA class II, III or IV,
    ii) an elevated plasma BNP or NT-proBNP level, preferably a plasma BNP ≥100 pg/mL (or NT-proBNP ≥400 pg/mL), more preferably a plasma BNP ≥150 pg/mL or NT-proBNP ≥600 pg/mL, and
    iii) a reduced left ventricular ejection fraction (LVEF) of ≤40%, preferably ≤35%.

In addition, the patient might be characterized by one or more of the following:
    iv) prior hospitalization for heart failure within the last 12 months,
    v) a stable ACE inhibitor or ARB at dose ≥enalapril 10 mg daily+beta-blocker (unless contraindicated or intolerant)+aldosterone antagonist (as indicated),
    vi) systolic blood pressure ≥95 mm Hg,
    vii) eGFR ≥30 ml/min/1.73 m² and
    viii) serum K ≤5 5.4 mEq/L.

In another embodiment of the foregoing, the patient has heart failure classified as NYHA class II, III or IV and has systolic dysfunction. In another embodiment the patient has heart failure classified as NYHA class II. In a further embodiment, the patient has heart failure classified as NYHA class II with systolic dysfunction and has a reduced left ventricular ejection fraction (LVEF) of ≤35%.

All the aforementioned embodiments for the methods of protection and treatment according to the present invention are equally applicable to
    the use of a compound of formula (I) or of the combination (i)/(ii) as defined herein for the manufacture of a medicament for use according to the present invention,
    the use of a compound of formula (I) or of the combination (i)/(ii) as defined herein according to the present invention,
    a compound of formula (I) or of the combination (i)/(ii) as defined herein for use according to the present invention,
    the pharmaceutical compositions comprising a compound of formula (I) or of the combination (i)/(ii) as defined herein for the use according to the present invention,
    the use of the pharmaceutical compositions comprising a compound of formula (I) or of the combination (i)/(ii) as defined herein according to the present invention and
    the use of the pharmaceutical compositions comprising a compound of formula (I) or of the combination (i)/(ii) as defined herein for the manufacture of a medicament for use according to the present invention.

Some of these aspects are further described in more detail below, but this description should not be construed as limiting.

Compound or Combination for Use

In a separate aspect, the present invention is directed to the following embodiment 20:

A twice-daily target dose of 200 mg of sacubitril and valsartan in a 1:1 molar ratio for use in the treatment of heart failure in a patient, wherein said dose is reached after a titration with an initial twice-daily dose of at least 50 mg of sacubitril and valsartan in a 1:1 molar ratio increasing to the twice daily target dose of 200 mg for from about 2 to about 8 weeks.

The invention is further described in the following embodiments, numbered 22 to 40:

22. The twice-daily target dose of embodiment 21 for use in the treatment of heart failure in a patient, wherein said dose is reached after a titration with a twice daily starting dose of 50 mg of sacubitril and valsartan in a 1:1 molar ratio for from about 2 weeks to about 4 weeks, followed by a twice daily dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

23. The twice-daily target dose of embodiment 22 for use in the treatment of heart failure in a patient, wherein said dose is reached after a titration with a twice daily starting dose of 50 mg of sacubitril and valsartan in a 1:1 molar ratio for from about 2 weeks to about 3 weeks, followed by a twice daily dose of 100 mg of sacubitril and valsartan in a 1:1 molar ratio for about 3 weeks, followed by the twice daily target dose of 200 mg of sacubitril and valsartan in a 1:1 molar ratio thereafter.

24. The twice daily target dose of embodiment 21 for use in the treatment of heart failure in a patient, wherein said dose is reached after a titration of a twice daily starting dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

25. The twice daily target dose of embodiment 24 for use in the treatment of heart failure in a patient, wherein said dose is reached after a titration of a twice daily starting dose of 100 mg of sacubitril and valsartan in a 1:1 molar ratio for about 2 weeks, followed by the twice daily target dose of 200 mg of sacubitril and valsartan in a 1:1 molar ratio thereafter.

26. The twice daily target dose of embodiment 22 or 23 for use in the treatment of heart failure in a patient, wherein the twice daily starting dose of 50 mg of sacubitril and valsartan in a 1:1 molar ratio is for use in a patient not taking an angiotensin-converting enzyme (ACE) inhibitor or an angiotensin II receptor blocker (ARB) before initiating the treatment with sacubitril and valsartan.

27. The twice daily target dose of embodiment 22 for use in the treatment of heart failure in a patient, wherein the twice daily starting dose of 50 mg of sacubitril and valsartan in a 1:1 molar ratio is for use in a patient taking low doses of an angiotensin-converting enzyme (ACE) inhibitor or of an angiotensin II receptor blocker (ARB) before initiating the treatment with sacubitril and valsartan.

28. The twice daily target dose of embodiment 27 for use in the treatment of heart failure in a patient, wherein the lower dose of an ACEI or ARB is equivalent to ≤10 mg of enalapril per day.

29. The twice daily target dose of embodiment 21 for use in the treatment of heart failure in a patient, wherein said titration mitigates a risk selected from hypotension, hyperkalemia, and renal adverse events.

30. The twice daily target dose of embodiment 4 or 5 for use in the treatment of heart failure in a patient, wherein the twice daily starting dose of 100 mg of sacubitril and valsartan in a 1:1 molar ratio is for use in a patient taking higher doses of an angiotensin-converting enzyme (ACE) inhibitor or of an angiotensin II receptor blocker (ARB) before initiating the treatment with sacubitril and valsartan.

31. The twice daily target dose of embodiment 30 for use in the treatment of heart failure in a patient, wherein the higher dose of an ACEI or ARB is equivalent to ≥10 mg of enalapril per day.

32. The twice-daily target dose of any one of the preceding embodiments 21 to 31 for use in the treatment of heart failure in a patient, wherein the patient suffers from chronic systolic heart failure with reduced ejection fraction.

33. The twice-daily target dose of any one of the preceding embodiments 21 to 31 for use in the treatment of heart failure in a patient, wherein the patient is a human patient.

34. The twice-daily target dose of any one of the preceding embodiments 21 to 31 for use in the treatment of heart failure in a patient, wherein the patient has at least one of the following characteristics
   i) heart failure of NYHA class II, III or IV,
   ii) an elevated plasma BNP or NT-proBNP level, preferably a plasma BNP ≥100 pg/mL (or NT-proBNP ≥400 pg/mL), more preferably a plasma BNP ≥150 pg/mL or NT-proBNP ≥600 pg/mL, and
   iii) a reduced left ventricular ejection fraction (LVEF) of ≤40%, preferably ≤35%.

35. The twice-daily target dose of any one of the preceding embodiments 21 to 31 for use in the treatment of heart failure in a patient, wherein the patient suffers from chronic heart failure classified as NYHA class II, III or IV and has systolic dysfunction, preferably wherein the patient has a reduced left ventricular ejection fraction (LVEF) of ≤35%.

36. The twice-daily target dose of any one of the preceding embodiments 21 to 31 for use in the treatment of heart failure in a patient, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino) butyrate] hemipentahydrate (LCZ696).

37. The twice-daily target dose of any one of the preceding embodiments 21 to 31 for use in the treatment of heart failure in a patient, wherein sacubitril and valsartan in a 1:1 molar ratio are delivered in the form of a pharmaceutical composition comprising
   (i) valsartan or a pharmaceutically acceptable salt thereof; and
   (ii) sacubitril or a pharmaceutically acceptable salt thereof, 38. The twice-daily target dose of any one of the preceding embodiments 21 to 31 for use in the treatment of heart failure in a patient, wherein the patient receives a base treatment with a stable dose of a beta-blocker, an aldosterone antagonists, and/or a diuretic.

39. The twice-daily target dose of any one of the preceding embodiments 21 to 31 for use in the treatment of heart failure in a patient, wherein the patient has to stop taking the angiotensin receptor blocker (ARB) or the ACE inhibitor at least 36 hours prior to taking the medicament.

40. The twice-daily target dose of any one of the preceding embodiments 21 to 31 for use in the treatment of heart failure in a patient, wherein
   a) the 50 mg dose of sacubitril and valsartan in a 1:1 molar ratio corresponds to 24 mg sacubitril and 26 mg valsartan,
   b) the 100 mg dose of sacubitril and valsartan in a 1:1 molar ratio corresponds to 49 mg sacubitril and 51 mg valsartan, and
   c) the 200 mg dose of sacubitril and valsartan in a 1:1 molar ratio corresponds to 97 mg sacubitril and 103 mg valsartan.

Use for the Manufacture of a Medicament

In a separate aspect, the present invention is directed to the following embodiment 41:

41. Use of sacubitril and valsartan in a 1:1 molar ratio for the manufacture of a medicament for the treatment of heart failure in a patient, wherein the medicament comprises a twice-daily target dose of 200 mg of sacubitril and valsartan in a 1:1 molar ratio which is reached after a titration with an initial twice-daily dose of at least 50 mg of sacubitril and valsartan in a 1:1 molar ratio increasing to the twice daily target dose of 200 mg for from about 2 to about 8 weeks.

The invention is further described in the following embodiments, numbered 42 to 61:

42. Use of sacubitril and valsartan in a 1:1 molar ratio for the manufacture of a medicament for the treatment of heart failure in a patient according to embodiment 41, wherein said target dose is reached after a titration with a twice daily starting dose of 50 mg of sacubitril and valsartan in a 1:1 molar ratio for from about 2 weeks to about 4 weeks, followed by a twice daily dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

43. Use of sacubitril and valsartan in a 1:1 molar ratio for the manufacture of a medicament for the treatment of heart failure in a patient according to embodiment 42, wherein said target dose is reached after a titration with a twice daily starting dose of 50 mg of sacubitril and valsartan in a 1:1 molar ratio for from about 2 weeks to about 3 weeks, followed by a twice daily dose of 100 mg of sacubitril and valsartan in a 1:1 molar ratio for about 3 weeks, followed by the twice daily target dose of 200 mg of sacubitril and valsartan in a 1:1 molar ratio thereafter.

44. Use of sacubitril and valsartan in a 1:1 molar ratio for the manufacture of a medicament for the treatment of heart failure in a patient according to embodiment 41, wherein said target dose is reached after a titration of a twice daily starting dose of 100 mg of sacubitril and valsartan in a 1:1 molar ratio for from about 2 weeks to about 4 weeks, followed by the twice daily target dose of 200 mg of sacubitril and valsartan in a 1:1 molar ratio thereafter.

45. Use of sacubitril and valsartan in a 1:1 molar ratio for the manufacture of a medicament for the treatment of heart failure in a patient according to embodiment 44, wherein said target dose is reached after a titration of a twice daily starting dose of 100 mg of sacubitril and valsartan in a 1:1 molar ratio for about 2 weeks, followed by the twice daily target dose of 200 mg of sacubitril and valsartan in a 1:1 molar ratio thereafter.

46. Use of sacubitril and valsartan in a 1:1 molar ratio for the manufacture of a medicament for the treatment of heart failure in a patient according to embodiment 42 or 43, wherein the twice daily starting dose of 50 mg of sacubitril and valsartan in a 1:1 molar ratio is for use in a patient not taking an angiotensin-converting enzyme (ACE) inhibitor or an angiotensin II receptor blocker (ARB) before initiating the treatment with sacubitril and valsartan.

47. Use of sacubitril and valsartan in a 1:1 molar ratio for the manufacture of a medicament for the treatment of heart failure in a patient according to embodiment 42 or 43, wherein the twice daily starting dose of 50 mg of sacubitril and valsartan in a 1:1 molar ratio is for use in a patient taking low doses of an angiotensin-converting enzyme (ACE) inhibitor or of an angiotensin II receptor blocker (ARB) before initiating the treatment with sacubitril and valsartan.

48. Use of sacubitril and valsartan in a 1:1 molar ratio for the manufacture of a medicament for the treatment of heart failure in a patient according to embodiment 47, wherein the lower dose of an ACEI or ARB is equivalent to ≤10 mg of enalapril per day.

49. Use of sacubitril and valsartan in a 1:1 molar ratio for the manufacture of a medicament for the treatment of heart failure in a patient according to embodiment 41, wherein said titration mitigates a risk selected from hypotension, hyperkalemia, and renal adverse events.

50. Use of sacubitril and valsartan in a 1:1 molar ratio for the manufacture of a medicament for the treatment of heart failure in a patient according to embodiment 44 or 45, wherein the twice daily starting dose of 100 mg of sacubitril and valsartan in a 1:1 molar ratio is for use in a patient taking higher doses of an angiotensin-converting enzyme (ACE) inhibitor or of an angiotensin II receptor blocker (ARB) before initiating the treatment with sacubitril and valsartan.

51. Use of sacubitril and valsartan in a 1:1 molar ratio for the manufacture of a medicament for the treatment of heart failure in a patient according to embodiment 50, wherein the higher dose of an ACEI or ARB is equivalent to ≥10 mg of enalapril per day.

52. Use of sacubitril and valsartan in a 1:1 molar ratio for the manufacture of a medicament for the treatment of heart failure in a patient according to any one of the preceding embodiments 41 to 51, wherein the patient suffers from chronic systolic heart failure with reduced ejection fraction.

53. Use of sacubitril and valsartan in a 1:1 molar ratio for the manufacture of a medicament for the treatment of heart failure in a patient according to any one of the preceding claims 41 to 51, wherein the patient is a human patient.

54. Use of sacubitril and valsartan in a 1:1 molar ratio for the manufacture of a medicament for the treatment of heart failure in a patient according to any one of the preceding embodiments 41 to 51, wherein the patient has at least one of the following characteristics
   i) heart failure of NYHA class II, III or IV,
   ii) an elevated plasma BNP or NT-proBNP level, preferably a plasma BNP ≥100 pg/mL (or NT-proBNP ≥400 pg/mL), more preferably a plasma BNP ≥150 pg/mL or NT-proBNP ≥600 pg/mL, and
   iii) a reduced left ventricular ejection fraction (LVEF) of ≤40%, preferably ≤35%.

55. Use of sacubitril and valsartan in a 1:1 molar ratio for the manufacture of a medicament for the treatment of heart failure in a patient according to any one of the preceding embodiments 41 to 51, wherein the patient suffers from chronic heart failure classified as NYHA class II, III or IV and has systolic dysfunction, preferably wherein the patient has a reduced left ventricular ejection fraction (LVEF) of ≤35%.

56. Use of sacubitril and valsartan in a 1:1 molar ratio for the manufacture of a medicament for the treatment of heart failure in a patient according to any one of the preceding embodiments 41 to 51, wherein sacubitril and valsartan in a 1:1 molar ratio are delivered in the form of the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696).

57. Use of sacubitril and valsartan in a 1:1 molar ratio for the manufacture of a medicament for the treatment of heart failure in a patient according to any one of the preceding embodiments 41 to 51, wherein sacubitril and valsartan in a 1:1 molar ratio are delivered in the form of a pharmaceutical composition comprising
   (i) valsartan or a pharmaceutically acceptable salt thereof; and
   (ii) sacubitril or a pharmaceutically acceptable salt thereof, 58. Use of sacubitril and valsartan in a 1:1 molar ratio for the manufacture of a medicament for the treatment of heart failure in a patient according to any one of the preceding embodiments 41 to 51, wherein the patient receives a base treatment with a stable dose of a beta-blocker, an aldosterone antagonists, and/or a diuretic.

59. Use of sacubitril and valsartan in a 1:1 molar ratio for the manufacture of a medicament for the treatment of heart failure in a patient according to any one of the preceding embodiments 41 to 51, wherein the patient receives base treatment with a stable dose of a beta-blocker and optionally an aldosterone antagonist.

60. Use of sacubitril and valsartan in a 1:1 molar ratio for the manufacture of a medicament for the treatment of heart failure in a patient according to any one of the preceding embodiments 41 to 51, wherein the patient has to stop taking the angiotensin receptor blocker (ARB) or the ACE inhibitor at least 36 hours prior to taking the medicament.

61. Use of sacubitril and valsartan in a 1:1 molar ratio for the manufacture of a medicament for the treatment of heart failure in a patient according to any one of the preceding embodiments 41 to 51, wherein a) the 50 mg dose of sacubitril and valsartan in a 1:1 molar ratio corresponds to 24 mg sacubitril and 26 mg valsartan,
b) the 100 mg dose of sacubitril and valsartan in a 1:1 molar ratio corresponds to 49 mg sacubitril and 51 mg valsartan, and
c) the 200 mg dose of sacubitril and valsartan in a 1:1 molar ratio corresponds to 97 mg sacubitril and 103 mg valsartan.

Compounds and Combinations and Pharmaceutical Compositions for Use According to the Invention The "sacubitril and valsartan in a 1:1 molar ratio" of the invention used in the aforementioned methods is provided in the form of
a) the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (LCZ696), or
b) a pharmaceutical composition comprising a 1:1 molar ratio of
(i) valsartan or a pharmaceutically acceptable salt thereof; and
(ii) of sacubitril or a pharmaceutically acceptable salt thereof.

Sacubitril is the INN for N-(3-carboxy-1-oxopropyl)-(4S)-(p-phenylphenylmethyl)-4-amino-2R-methylbutanoic acid ethyl ester. This is a prodrug for (2R,4S)-5-biphenyl-4-yl-4-(3-carboxy-propionyl amino)-2-methyl-pentanoic acid.

In a preferred embodiment, the compound trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is present in crystalline form.

In another embodiment, the combination comprises a 1:1 molar ratio
(i) of valsartan; and
(ii) of sacubitril or a pharmaceutically acceptable salt thereof, such as sodium or calcium salt.

In a preferred embodiment, the invention encompasses a pharmaceutical composition for use comprising a therapeutically effective amount of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate (Compound LCZ696). Such compounds and pharmaceutical compositions have been previously disclosed in WO2007/056546 and WO 2009/061713, whose preparative teachings are incorporated herein by reference.

In a further embodiment of the invention, the pharmaceutical compositions for use according to the present invention comprise trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate (LCZ696) and deliver upon administration the NEP inhibitor pro-drug sacubitril and the angiotensin receptor blocker valsartan together to the patient.

In one embodiment of the invention for all of its uses, the pharmaceutical composition comprises the the NEP inhibitor pro-drug sacubitril, namely N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof. Such combinations are for example disclosed within international patent application WO 2003/059345, which is herewith incorporated by reference.

In one embodiment, the pharmaceutical composition comprises the NEP inhibitor pro-drug sacubitril, namely N-(3-carboxy-1-oxopropyl)-(4S)-p-phenylphenylmethyl)-4-amino-(2R)-methylbutanoic acid ethyl ester or the NEP inhibitor N-(3-carboxy-1-oxopropyl)-(4S)-p-phenylphenylmethyl)-4-amino-(2R)-methylbutanoic acid, or pharmaceutically acceptable salts thereof, and the Angiotensin Receptor Blocker valsartan or a pharmaceutically acceptable salt thereof, in a 1:1 molar ratio.

(i) Valsartan or (S)—N-valeryl-N-{[2'-(1H-tetrazole-5-yl)-biphenyl-4-yl]-methyl}-valine) or a pharmaceutically acceptable salt thereof that can be purchased from commercial sources or can be prepared according to known methods, such as described in U.S. Pat. No. 5,399,578 and EP 0443983, whose preparative teachings are incorporated by reference herein. Valsartan may be used in certain embodiments of the invention in its free acid form, as well as in any suitable salt form. Depending upon the circumstance, esters or other derivatives of the carboxylic grouping may be employed as well as salts and derivatives of the tetrazole grouping.

(ii) sacubitril, namely N-(3-carboxy-1-oxopropyl)-(4S)-(p-phenylphenylmethyl)-4-amino-2R-methylbutanoic acid ethyl ester, or (2R,4S)-5-biphenyl-4-yl-4(3-carboxy-propionyl amino)-2-methyl-pentanoic acid can be prepared by known methods such as described in U.S. Pat. No. 5,217,996 which is herein incorporated by reference.

The corresponding active ingredient or a pharmaceutically acceptable salt thereof may also be used in the form of a hydrate or include other solvents used for crystallization.

The pharmaceutical compositions according to the invention can be prepared in a manner known per se and are those suitable for enteral, such as oral or rectal, and parenteral administration to mammals (warm-blooded animals), including man, comprising a therapeutically effective amount of the pharmacologically active compound, alone or in combination with one or more pharmaceutically acceptable carriers, especially suitable for enteral or parenteral application.

The pharmaceutical preparations of the invention contain, for example, from about 0.1% to about 100%, e.g. 80% or 90%, or from about 1% to about 60%, of the active ingredient. The term "about" or "approximately", as used herein in each instance, shall have the meaning of within 10%, more preferably within 5%, of a given value or range.

Pharmaceutical preparations according to the invention for enteral or parenteral administration are, e.g., those in unit dose forms, such as sugar-coated tablets, tablets, capsules, bars, sachets, granules, syrups, aqueous or oily suspensions or suppositories and furthermore ampoules. These are prepared in a manner known per se, e.g. by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Tablets may be formed from the active compound with fillers, for example calcium phosphate; disintegrating agents, for example maize starch, lubricating agents, for example magnesium stearate; binders, for example microcrystalline cellulose or polyvinylpyrrolidone and other optional ingredients known in the art to permit tabletting the mixture by known methods. Similarly, capsules, for example hard or soft gelatin capsules, containing the active compound with or without added excipients, may be prepared by known methods. The contents of the capsule may be formulated using known methods so as to give sustained release of the active compound.

Other dosage forms for oral administration include, for example, aqueous suspensions containing the active compound in an aqueous medium in the presence of a non-toxic suspending agent such as sodium carboxymethylcellulose, and oily suspensions containing the active compounds in a suitable vegetable oil, for example *arachis* oil.

The active compound may be formulated into granules with or without additional excipients. The granules may be ingested directly by the patient or they may be added to a suitable liquid carrier (e.g. water) before ingestion. The granules may contain disintegrants, e.g. an effervescent pair formed from an acid and a carbonate or bicarbonate salt to facilitate dispersion in the liquid medium.

The dosage of the active ingredient of the composition will, of course, vary with the nature of the severity of the condition to be treated and with the particular compound in the composition and its route of administration. It will also vary according to the age, weight and response of the individual patient.

In the embodiments where the pharmaceutical composition comprises trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate (LCZ696) in the pharmaceutical compositions for use in the context of the present invention, the unit dose of the therapeutic agents sacubitril and valsartan together will be in the range from about 1 to about 1000 mg, such as 40 mg to 400 mg (e.g., 50 mg, 100 mg, 200 mg, 400 mg) per day. Alternatively lower doses may be given, for example doses of 0.5 to 100 mg; 0.5 to 50 mg; or 0.5 to 20 mg per day. As explanatory note, a unit dose of 100 mg LCZ696 delivering 100 mg of the two agents sacubitril and valsartan corresponds to 113.1 mg of trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate]hemipentahydrate. Correspondingly, a unit dose of 200 mg requires 226.2 mg, and a unit dose of 400 mg requires 452.4 mg of trisodium [3-((1 S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino) butyrate]hemipentahydrate.

Dosages of the sum of the individual compounds (i)/(ii) in the combination of the pharmaceutical composition will be in the range from about 1 to about 1000 mg, such as 40 mg to 400 mg and include but are not limited to 5 mg, 20 mg, 25 mg, 40 mg, 50 mg, 80 mg, 100 mg, 200 mg, 400 mg, 800 mg and 1000 mg. Such dosages for compounds (i)/(ii) can be considered therapeutically effective amounts or dosage strengths. Ratios for the amount of each compound in the pharmaceutical composition are preferably in the about 1:1 molar ratio to achieve an optimal renal protection while still providing cardiovascular benefits. In preferred embodiments, the dosages of the individual compounds (i)/(ii) correspond to the same molecular amounts as in a pharmaceutical composition comprising a 50 mg, 100 mg, 200 mg or 400 mg dose of LCZ696. E.g. a 200 mg dose of LCZ696 corresponds approximately to 103 mg valsartan and 97 mg of sacubitril Pharmaceutical compositions containing a compound of formula (I) (such as compound LCZ696), or compounds (i)/(ii) can be administered any number of times per day, i.e. once a day (q.d.), twice (b.i.d.), three times, four time, etc. in an immediate release formation or less frequently as an extended or sustained release formation. Preferably the pharmaceutical composition is administered twice daily (b.i.d.). Corresponding doses may be taken, for example, in the morning, at mid-day or in the evening.

The following example is illustrative, but does not serve to limit the scope of the invention described herein.

EXAMPLE

A multicenter, randomized, double-blind, parallel group study to assess the safety and tolerability of initiating LCZ696 in heart failure patients comparing two titration regimens.

Study Drug LCZ696:

LCZ696 refers to the supramolecular complex trisodium [3-((1S,3R)-1-biphenyl-4-ylmethyl-3-ethoxycarbonyl-1-butylcarbamoyl) propionate-(S)-3'-methyl-2'-(pentanoyl{2"-(tetrazol-5-ylate)biphenyl-4'-ylmethyl}amino)butyrate] hemipentahydrate. This compound and pharmaceutical compositions thereof have been previously disclosed in WO2007/056546 and WO 2009/061713, whose preparative teachings are incorporated herein by reference.

LCZ696 is a first-in-class angiotensin receptor neprilysin inhibitor that comprises the molecular moieties of the NEP (neutral endopeptidase EC 3.4.24.11) inhibitor pro-drug sacubitril (INN, also known as AHU377 and N-(3-carboxy-1-oxopropyl)-(4S)-p-phenylphenylmethyl)-4-amino-(2R)-methylbutanoic acid ethyl ester) and the angiotensin receptor blocker valsartan as a single compound. Sacubitril is metabolized by enzymatic cleavage to LBQ657 (N-(3-carboxy-1-oxopropyl)-(4S)-p-phenylphenylmethyl)-4-amino-(2R)-methylbutanoic acid), the active inhibitor of neutral endopeptidase, which is the major enzyme responsible for the breakdown of atrial natriuretic peptides.

Overall Study Design

This was a multicenter, randomized, double-blind, parallel group study to assess the safety and tolerability of initiating LCZ696 in heart failure patients (New York Heart Association [NYHA] class II-IV) with reduced ejection fraction defined by a left ventricular ejection fraction (LVEF)≤35%. Up-titration regimens of 3-weeks or 6-weeks to the LCZ696 target dose of 200 mg bid were evaluated. The study consisted of two main phases: (1) open-label LCZ696 run-in phase lasting approximately one week, and (2) double-blind randomized phase lasting approximately 11 weeks. Patients enrolled were stratified based on the pre-study level of RAAS inhibition (high/low).

Study Objectives

Primary Objectives

To characterize the safety and tolerability of initiating LCZ696 in HFrEF patients with 3-week and 6-week up-titration regimens over 12 weeks based on reported adverse events and laboratory assessments.

Secondary Objectives

The secondary objectives were:
- To evaluate the proportion of patients in the two treatment groups who achieved treatment success, defined as those achieving and maintaining LCZ696 200 mg bid without any dose interruption or down-titration over 12 weeks.
- To evaluate the proportion of patients who tolerate a regimen of LCZ696 200 mg bid for at least 2 weeks leading to study completion, regardless of previous dose interruption or down-titration.

Study Design

This was a multi-center, randomized, double-blind, parallel-group study conducted to evaluate the safety and tolerability of LCZ696 comparing two up-titration regimens in both outpatients and hospitalized patients (inpatients) with HFrEF.

Patients were stratified based on the level of RAAS inhibition as follows:

High RAAS stratum: Patients receiving >160 mg of valsartan or >10 mg total daily dose of enalapril, or equivalent doses of other ARBs/ACEIs, respectively, at screening Low RAAS stratum: Patients receiving ≤160 mg of valsartan or ≤10 mg total daily dose of enalapril, or equivalent doses of other ARBs/ACEIs, respectively, at screening. This stratum also included patients who were not on an ACEI or an ARB 4 weeks prior to screening (i.e., ACEI/ARB-naïve patients)

At least 25% (but not more than 50%) of the randomized patients were planned to be in the low RAAS inhibition stratum. Patients hospitalized for decompensated HF were allowed to enter either the low or high RAAS inhibition stratum, corresponding to the most recent tolerated ACEI or ARB dose they had received during their hospitalization.

Figure 1:
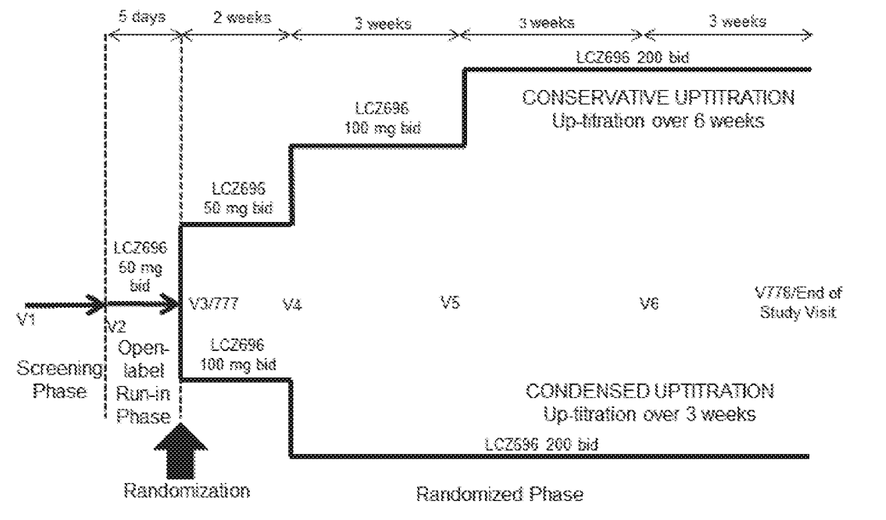
FIG. 1 shows the study design for the multi-center, randomized, double-blind, parallel-group study conducted to evaluate the safety and tolerability of LCZ696 comparing two up-titration regimens in both outpatients and hospitalized patients (inpatients) with HFrEF.

This study consisted of three phases: see FIG. 1.
(1) Screening phase lasting approximately one week;
(2) Open-label LCZ696 run-in phase lasting approximately one week (Day 1 to 5); and
(3) Randomized phase lasting approximately 11 weeks Screening Phase At Visit 1, during the screening phase, all patients who had provided their written informed consent were evaluated for eligibility to enter the study. Left ventricular ejection fraction (LVEF) measurements required for eligibility were based on locally obtained echocardiograms, MUGA (multi-gated acquisition) scans, CT (computerized tomography) scans, MRI (magnetic resonance imaging) scans, or ventricular angiographies performed within the prior 12 months, provided no subsequent measurements were >35%. If a LVEF measurement from the prior 12 months was not available, the patient could enter the trial based on a LVEF ≤35% obtained during the screening phase, i.e., before start of study medication intake. If a patient had an implanted cardiac resynchronization therapy (CRT) device, the LVEF value used to qualify for the study had to be obtained by at least three months after device implantation.

Both inpatients and outpatients were eligible for participation in this study. Patients who met all the eligibility criteria at screening were eligible to enter the open-label LCZ696 run-in phase and proceed to Visit 2 to start receiving the study medication. Patients who had been using ACEIs had to stop these medications under the supervision of the study investigator, and enter a 36-hour ACEI-free washout period before they attended their Visit 2.

Open-Label LCZ696 Run-in Phase

Patients who met all the entry criteria and completed the ACEI-free washout period (if required) attended Visit 2 within approximately one week after Visit 1. At Visit 2, patients began taking open-label LCZ696 50 mg bid. Eligible hospitalized patients also took the study medication while they were still in the hospital and before they were discharged. Patients took the study medication in addition to their background HF therapy, except for ACEIs and ARBs, which were replaced by the study medication.

Patients were asked to return after 5±2 days to attend Visit 3/777 (Randomization visit).

Randomized Phase

At Visit 3/777, safety and tolerability of LCZ696 50 mg bid was assessed (see table below). Patients, who could not tolerate LCZ696 50 mg bid per the criteria listed in the Table, were to be discontinued from the study and considered as run-in failures.

TABLE

Safety criteria that must be met at Visits 3 to 6 in order to avoid treatment failure

| Parameter | Requirement |
|---|---|
| Potassium level | ≤5.4 mmol/L |
| Kidney function | eGFR ≥30 mL/min/1.73 m$^2$ |
|  | eGFR reduction ≤35% compared to Screening value |
| Blood pressure | No symptomatic hypotension and SBP ≥95 mmHg |
| Adverse events (AEs) or conditions | No postural symptoms or any AEs that preclude continuation according to the investigator's judgment |

Patients who successfully completed the open-label run-in and tolerated LCZ696 50 mg bid were to be randomized to receive double-blind LCZ696 at one of the two different titration schemes in a 1:1 ratio: they could be up-titrated to 200 mg bid over the following two weeks (Condensed titration) or they could be up-titrated to 200 mg bid over the following five weeks (Conservative titration).

At Visit 3/777, patients randomized to the condensed up-titration arm were up-titrated to LCZ696 100 mg bid, while patients randomized to the conservative up-titration arm continued to receive LCZ696 50 mg bid.

Two weeks after Visit 3/777, at Visit 4, the patients who were judged by the investigator to be tolerant of the study medication per the safety criteria in the Table were up-titrated to the next dose level; those in the condensed up-titration arm received LCZ696 200 mg bid and those in the conservative up-titration arm received LCZ696 100 mg bid.

Patients returned three weeks later to attend Visit 5. Patients who were judged by the investigator to be tolerant of the study medication per the safety criteria in the Table further continued on the titration plan as outlined in above; patients in the condensed up-titration arm continued to receive LCZ696 200 mg bid, while patients in the conservative up-titration arm were up-titrated to LCZ696 200 mg bid.

Patients returned three weeks later to attend Visit 6. Patients who were judged by the investigator to be tolerant of the study medication per the safety criteria in the Table continued to receive LCZ696 200 mg bid and were asked to return three weeks later to attend Visit 778/End of Study (EoS) to undergo the final safety evaluations.

Patients who were deemed by the investigator to require dose reduction or interruption in study medication dosing at any post-randomization visit (despite modification of concomitant medications) were considered as treatment failures. They were switched to open-label LCZ696 at a dose level at the discretion of the investigator. Treatment failure patients were expected to attend the remaining study visits according to schedule and their doses were modified based on the investigator's judgment with the overall goal of achieving and maintaining the target dose (LCZ696 200 mg bid) for at least two uninterrupted weeks and until Visit 778/EoS.

Throughout the randomized phase, patients took the study medication in addition to their background HF therapy, except for ACEIs and ARBs, which were replaced by the study medication itself. Every attempt was made to maintain patients on the assigned study medication throughout the trial.

At each visit, the patients' medication compliance as well as safety and tolerability of the study medication was assessed, including, but not limited to, signs and symptoms of hypotension, elevated potassium level, and decreased renal function. If, however, in the opinion of the investigator, the patient could not tolerate the assigned study medication, the investigator could consider if the non-disease-modifying medications (e.g., CCBs, diuretics, nitrates, a-blockers) could be reduced to manage tolerability before declaring the patient to be a treatment failure and subsequently switching him/her to open-label study medication. The investigator was also allowed to adjust doses of other disease-modifying medications if they were believed to be the most likely cause of the adverse effects.

Patients

Written informed consent was obtained before any assessment was performed.

Patients eligible for inclusion in this study must have fulfilled all of the following criteria listed below:
1. Males and/or females of at least 18 years of age, who were either inpatients or outpatients
2. Diagnosis of chronic heart failure (CHF) NYHA class II-IV.
3. Left ventricular ejection fraction (LVEF)≤35% at screening (any local measurement made within the past 12 months using echocardiography, MUGA, CT scanning, MRI, or ventricular angiography was acceptable, provided no subsequent measurement was >35%).
4. Meeting one of the following criteria:
   ACEI/ARB naïve patients, i.e., not on an ACEI or ARB for at least 4 weeks before screening.
   For outpatients who were being treated with ACEI or ARB, dose had to be stable dose for at least 2 weeks before screening.
   For hospitalized patients (inpatients), being on no ACEI/ARB or on a tolerated dose of an ACEI or an ARB at screening.
5. Patients treated with a β-blocker, unless contraindicated or not tolerated (reason had to be documented in absence of that medication).
6. An aldosterone antagonist was also to be considered in all patients, taking account of renal function, serum potassium and tolerability. If given, the dose of aldosterone antagonist was to be optimized according to guideline recommendations and patient tolerability. Other evidence-based therapy for HF was also to be considered, e.g., cardiac resynchronization therapy and an implantable cardioverter-defibrillator in selected patients, as recommended by guidelines.

Treatment Arms

Patients were assigned to one of the following two treatment arms in a ratio of 1:1 as described below:
   Condensed up-titration: up-titration of LCZ696 from 50 mg bid to 200 mg bid over three weeks (including the run-in phase).
   Conservative up-titration: up-titration of LCZ696 from 50 mg bid to 200 mg bid over six weeks (including the run-in phase).

REFERENCE

The study design and procedures can be found under www.clinicaltrials.gov, study number NCT01922089, which is herewith incorporated by reference.

Results
Summary:

Among the randomized patients and excluding those who discontinued due to non-AE related reasons, 81% achieved the target LCZ696 200 mg bid dose without any down-titration or dose interruption over the entire 12-week study period, and 85% were on the LCZ696 200 mg bid target dose for at least 2 weeks before study completion. The most common reasons for dose adjustment/interruption or permanent discontinuation were AEs related to hypotension, renal dysfunction or hyperkalemia.

During the randomized period, a higher proportion of low RAAS stratum patients achieved the LCZ696 200 mg bid target dose and had no dose adjustment/interruption over 12 weeks if they were up-titrated more gradually. Eight-five percent (85%) of patients who were ACEI/ARB naïve or receiving prior low levels of RAAS therapy and up-titrated over 6 weeks achieved the target dose of LCZ696 200 mg bid and had no dose adjustment/interruption over 12 weeks compared with 74% of patients up-titrated over 3 weeks. This difference was due to fewer AEs related to hypotension, renal dysfunction or hyperkalemia. Eighty-three percent (83%) of patients receiving prior high levels of RAAS therapy achieved the LCZ696 200 mg bid target dose without any dose adjustment/interruption over 12 weeks, with no difference due to the rate of up-titration (3 vs. 6 weeks). There was no major difference between the uptitration regimens in the treatment success rate among the ACEI/ARB-naïve patients.

CONCLUSION

Across both run-in and randomized periods, the proportion of patients who achieved the target dose of LCZ696 200 mg bid without any dose adjustment or interruption over 12 weeks was 76% if discontinuations due to non-AE reasons are excluded and 70% based on the total number of patients receiving at least one dose of study medication.

In the low dose stratum, the rate of treatment success was higher when LCZ696 was uptitrated more gradually.

The invention claimed is:

1. A regimen for treating chronic heart failure with reduced ejection fraction, which comprises administering to a human patient in need thereof a twice-daily target dose of 200 mg of sacubitril or a pharmaceutically acceptable salt thereof with valsartan or a pharmaceutically acceptable salt thereof, which are provided to the human patient in a 1:1 molar ratio, wherein the twice daily target dose of 200 mg corresponds to 97 mg of sacubitril and 103 mg of valsartan;
   wherein the twice daily target dose 200 mg is reached after a titration with a twice daily starting dose of 50 mg of sacubitril or the pharmaceutically acceptable salt thereof together with valsartan or the pharmaceutically acceptable salt thereof, which are provided to the human patient in a 1:1 molar ratio, for from about 3 weeks to about 4 weeks, wherein the twice daily starting dose of 50 mg corresponds to 24 mg of sacubitril and 26 mg of valsartan, followed by a twice daily dose of 100 mg of sacubitril or the pharmaceutically acceptable salt thereof together with valsartan or the pharmaceutically acceptable salt thereof, which are provided to the human patient in a 1:1 molar ratio, for from about 3 weeks to about 4 weeks, wherein the twice daily dose of 100 mg corresponds to 49 mg of sacubitril and 51 mg of valsartan, followed by the twice daily target dose of 200 mg thereafter; and
   wherein:

(i) the twice daily starting dose of 50 mg is for use in a human patient neither taking an angiotensin-converting enzyme (ACE) inhibitor nor taking an angiotensin II receptor blocker (ARB) before initiating treatment with sacubitril or the pharmaceutically acceptable salt thereof and valsartan or the pharmaceutically acceptable salt thereof, or (ii) the twice daily starting dose of 50 mg is for use in a human patient taking a low dose of an angiotensin-converting enzyme (ACE) inhibitor or a low dose of an angiotensin II receptor blocker (ARB) before initiating treatment with sacubitril or the pharmaceutically acceptable salt thereof and valsartan or the pharmaceutically acceptable salt thereof, wherein the low dose of the ACE inhibitor or the low dose of the ARB is equivalent to a dose of <10 mg of enalapril per day.

2. The regimen for treating chronic heart failure according to claim 1, wherein the twice daily target dose of 200 mg is reached after the titration with the twice daily starting dose of 50 mg for about 3 weeks, followed by the twice daily dose of 100 mg for about 3 weeks, followed by the twice daily target dose of 200 mg thereafter.

3. The regimen for treating chronic heart failure according to claim 1, wherein the human patient has to stop taking the ARB or the ACE inhibitor at least 36 hours before initiating the treatment with sacubitril or the pharmaceutically acceptable salt thereof and valsartan or the pharmaceutically acceptable salt thereof.

4. The regimen for treating chronic heart failure according to claim 1, wherein the human patient has an elevated plasma BNP of ≥100 pg/mL or NT-proBNP of ≥400 pg/mL.

5. The regimen for treating chronic heart failure according to claim 1, wherein the human patient has an elevated plasma BNP of ≥150 pg/mL or NT-proBNP of ≥600 pg/mL.

6. The regimen for treating chronic heart failure according to claim 1, wherein the human patient has a reduced left ventricular ejection fraction (LVEF) of ≤35%.

7. A regimen for treating chronic heart failure with reduced ejection fraction, which comprises administering to a human patient in need thereof a twice-daily target dose of 200 mg of sacubitril or a pharmaceutically acceptable salt thereof together with valsartan or a pharmaceutically acceptable salt thereof, which are provided to the human patient in a 1:1 molar ratio, wherein the twice daily target dose of 200 mg corresponds to 97 mg of sacubitril and 103 mg of valsartan;

wherein the twice daily target dose of 200 mg is reached after a titration with a twice daily starting dose of 50 mg of sacubitril or the pharmaceutically acceptable salt thereof together with valsartan or the pharmaceutically acceptable salt thereof, which are provided to the human patient in a 1:1 molar ratio, for from about 2 weeks to about 4 weeks, wherein the twice daily starting dose of 50 mg corresponds to 24 mg of sacubitril and 26 mg of valsartan, followed by a twice daily dose of 100 mg of sacubitril or the pharmaceutically acceptable salt thereof together with valsartan or the pharmaceutically acceptable salt thereof, which are provided to the human patient in a 1:1 molar ratio, for from about 2 weeks to about 4 weeks, wherein the twice daily target dose of 100 mg corresponds to 49 mg of sacubitril and 51 mg of valsartan, followed by the twice daily target dose of 200 mg thereafter, and wherein said titration to the target dose occurs over a period of at least about 6 weeks; and wherein:

(i) the twice daily starting dose of 50 mg is for use in a human patient neither taking an angiotensin-converting enzyme (ACE) inhibitor nor taking an angiotensin II receptor blocker (ARB) before initiating treatment with sacubitril or the pharmaceutically acceptable salt thereof and valsartan or the pharmaceutically acceptable salt thereof, or (ii) the twice daily starting dose of 50 mg is for use in a human patient taking a low dose of an angiotensin-converting enzyme (ACE) inhibitor or a low dose of an angiotensin II receptor blocker (ARB) before initiating treatment with sacubitril or the pharmaceutically acceptable salt thereof and valsartan or the pharmaceutically acceptable salt thereof, wherein the low dose of the ACE inhibitor or the low dose of the ARB is equivalent to a dose of <10 mg of enalapril per day.

8. The regimen for treating chronic heart failure according to claim 7, wherein the twice daily target dose is reached after the titration with the twice daily starting dose of 50 mg for about 3 weeks, followed by the twice daily dose of 100 mg for about 3 weeks, followed by the twice daily target dose of 200 mg thereafter.

9. The regimen for treating chronic heart failure according to claim 7, wherein the human patient has an elevated plasma BNP of ≥100 pg/mL or NT-proBNP of ≥400 pg/mL.

10. The regimen for treating chronic heart failure according to claim 7, wherein the human patient has an elevated plasma BNP of ≥150 pg/mL or NT-proBNP of ≥600 pg/mL.

11. The regimen for treating chronic heart failure according to claim 7, wherein the human patient has a reduced left ventricular ejection fraction (LVEF) of ≤35%.

12. The regimen for treating chronic heart failure according to claim 7, wherein the human patient has to stop taking the ARB or the ACE inhibitor at least 36 hours before initiating the treatment with sacubitril or the pharmaceutically acceptable salt thereof and valsartan or the pharmaceutically acceptable salt thereof.

13. The regimen for treating chronic heart failure according to claim 1, wherein the twice daily starting dose of 50 mg is for use in the human patient taking the low dose of the ACE inhibitor or the low dose of the ARB before initiating the treatment with sacubitril or the pharmaceutically acceptable salt thereof and valsartan or the pharmaceutically acceptable salt thereof.

14. The regimen for treating chronic heart failure according to claim 13, wherein the low dose of the ACE inhibitor or the low dose of the ARB is equivalent to the dose of <10 mg of enalapril per day.

15. The regimen for treating chronic heart failure according to claim 7, wherein the twice daily starting dose of 50 mg is for use in the human patient taking the low dose of the ACE inhibitor or the low dose of the ARB before initiating the treatment with sacubitril or the pharmaceutically acceptable salt thereof and valsartan or the pharmaceutically acceptable salt thereof.

16. The regimen for treating chronic heart failure according to claim 15, wherein the low dose of the ACE inhibitor or the low dose of the ARB is equivalent to the dose of <10 mg of enalapril per day.

17. The regimen for treating chronic heart failure according to claim 7, wherein a first week of the at least about 6 weeks is 5±2 days.

18. The regimen for treating chronic heart failure according to claim 1, wherein sacubitril or the pharmaceutically acceptable salt thereof together with valsartan or the pharmaceutically acceptable salt thereof are provided to the human patient in a 1:1 molar ratio by administering to the human patient a compound trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'- ylmethyl}amino)butyrate] hemipentahydrate (LCZ696).

19. The regimen for treating chronic heart failure according to claim 7, wherein sacubitril or the pharmaceutically acceptable salt thereof together with valsartan or the pharmaceutically acceptable salt thereof are provided to the human patient in a 1:1 molar ratio by administering to the human patient a compound trisodium [3-((1S,3R)-1-biphenyl-4-ylmethyl-3-ethoxycarbonyl-1-butylcarbamoyl)propionate-(S)-3'-methyl-2'- (pentanoyl{2''-(tetrazol-5-ylate)biphenyl-4'-ylmethyl}amino)butyrate] hemipentahydrate (LCZ696).

\* \* \* \* \*

UNITED STATES PATENT AND TRADEMARK OFFICE
CERTIFICATE OF CORRECTION

| | | |
|---|---|---|
| PATENT NO. | : 11,058,667 B2 | Page 1 of 1 |
| APPLICATION NO. | : 15/572399 | |
| DATED | : July 13, 2021 | |
| INVENTOR(S) | : Rizkala et al. | |

It is certified that error appears in the above-identified patent and that said Letters Patent is hereby corrected as shown below:

On the Title Page

<u>Item [56] REFERENCES CITED:</u>
"WO-2014029848" should read --WO 2014/029848--.

In the Specification

<u>Column 5:</u>
Line 20, "3-blockers" should read --β-blockers--.

<u>Column 15:</u>
Line 67, "sacubitril Pharmaceutical" should read --sacubitril. ¶Pharmaceutical--.

<u>Column 19:</u>
Line 14, "a-blockers)" should read --α-blockers)--.

In the Claims

<u>Column 20:</u>
Line 46, "thereof with" should read --thereof together with--; and
Line 50, "dose 200" should read --dose of 200--.

<u>Column 21:</u>
Line 16, "< 10 mg" should read "≤ 10 mg--; and
Line 62, "twice daily target dose of 100 mg" should read --twice daily dose of 100 mg--.

<u>Column 22:</u>
Line 16, "< 10 mg" should read --≤ 10 mg--.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*